United States Patent [19]
Tartaglia et al.

[11] Patent Number: 5,637,113
[45] Date of Patent: Jun. 10, 1997

[54] POLYMER FILM FOR WRAPPING A STENT STRUCTURE

[75] Inventors: Joseph M. Tartaglia, Redwood City; Joseph P. Loeffler; Todd H. Turnlund, both of Mountain View, all of Calif.

[73] Assignee: Advanced Cardiovascular Systems, Inc., Santa Clara, Calif.

[21] Appl. No.: 355,402

[22] Filed: Dec. 13, 1994

[51] Int. Cl.⁶ ............................................. A61F 2/06
[52] U.S. Cl. ............................ 623/1; 623/11; 604/104; 604/106; 604/194
[58] Field of Search ............... 623/1, 11; 606/191, 606/194; 604/104, 106

[56] References Cited

U.S. PATENT DOCUMENTS

| | | |
|---|---|---|
| 3,839,743 | 10/1974 | Schwarcz . |
| 4,346,028 | 8/1982 | Griffith . |
| 4,377,030 | 3/1983 | Beck et al. . |
| 4,633,873 | 1/1987 | Dumican et al. . |
| 4,656,083 | 4/1987 | Hoffman et al. . |
| 4,718,907 | 1/1988 | Karwoski et al. . |
| 4,722,335 | 2/1988 | Vilasi . |
| 4,723,549 | 2/1988 | Wholey et al. . |
| 4,732,152 | 3/1988 | Wallsten et al. . |
| 4,733,665 | 3/1988 | Palmaz . |
| 4,739,762 | 4/1988 | Palmaz . |
| 4,768,507 | 9/1988 | Fischell et al. . |
| 4,776,337 | 10/1988 | Palmaz . |
| 4,816,339 | 3/1989 | Tu et al. . |
| 4,878,906 | 11/1989 | Lindemann et al. . |
| 4,879,135 | 11/1989 | Greco et al. . |
| 4,994,298 | 2/1991 | Yasuda . |
| 5,019,090 | 5/1991 | Pinchuk . |

(List continued on next page.)

FOREIGN PATENT DOCUMENTS

| | | |
|---|---|---|
| 0 604 022 | 1/1994 | European Pat. Off. . |
| 0 578 998 | 6/1994 | European Pat. Off. . |
| 0 621 017 | 10/1994 | European Pat. Off. . |
| 0623354 | 11/1994 | European Pat. Off. . |
| 44 07 079 | 9/1994 | Germany . |
| WO91/17789 | 11/1991 | WIPO . |
| WO93/06792 | 4/1993 | WIPO . |
| WO-A-95 29647 | 11/1995 | WIPO . |

OTHER PUBLICATIONS

"IEEE Transactions on Biomedical Engineering," vol. BME-27, No. 11, Nov. 1980.

"Glow Discharge Polymers as Coatings for Implanted Devices," by Allen W. Hahn, et al., printed by John M. Dalton Research Center, University of Missouri (1981).

(List continued on next page.)

*Primary Examiner*—Paul B. Prebilic
*Attorney, Agent, or Firm*—Fulwider Patton Lee & Utecht

[57] ABSTRACT

The drug loaded stent includes an expandable stent structural member, and a planar sheet of polymeric material attached to the outside of the expandable stent structural member. The polymeric material is preferably bioabsorbable, and loaded or coated with a therapeutic agent or drug to reduce or prevent restenosis in the vessel being treated. The polymer material can be attached to the metal stent at one or more points, and wrapped in a coil around the stent in an unexpanded state, to uncoil and expand in diameter to substantially match the expanded diameter of the metal stent; or can be wrapped tightly around the stent structural member and attached to itself, to stretch radially when the stent structural member is expanded. In another currently preferred embodiment, a combination of a stent structural member and a polymeric film wrapping can be provided with a coating of lubricious material. The lubricious material can be polyethylene oxide, polyethylene glycol, polyethylene acetate, polyvinyl pyrrolidone, polyvinyl alcohol, polyacrylamide, hydrophilic soft segment urethanes, some natural gums, polyanhydrides or other similar hydrophilic polymers, and combinations thereof. The layer of lubricious material protects the stent from the guide or the body lumen in which the stent is inserted by providing a low friction surface over the stent.

10 Claims, 6 Drawing Sheets

U.S. PATENT DOCUMENTS

| | | |
|---|---|---|
| 5,059,211 | 10/1991 | Stack et al. . |
| 5,062,829 | 11/1991 | Pryor et al. . |
| 5,084,065 | 1/1992 | Weldon et al. . |
| 5,085,629 | 2/1992 | Goldberg et al. . |
| 5,108,755 | 4/1992 | Daniels et al. . |
| 5,123,917 | 6/1992 | Lee .............................................. 623/1 |
| 5,156,623 | 10/1992 | Hakamatsuka et al. . |
| 5,163,951 | 11/1992 | Pinchuk et al. . |
| 5,163,952 | 11/1992 | Froix . |
| 5,163,958 | 11/1992 | Pinchuk . |
| 5,192,311 | 3/1993 | King et al. . |
| 5,197,977 | 3/1993 | Hoffman, Jr. et al. . |
| 5,234,456 | 8/1993 | Silvestrini . |
| 5,234,457 | 8/1993 | Andersen . |
| 5,236,447 | 8/1993 | Kubo et al. . |
| 5,279,594 | 1/1994 | Jackson . |
| 5,282,860 | 2/1994 | Matsuno et al. . |
| 5,289,831 | 3/1994 | Bosley . |
| 5,290,271 | 3/1994 | Jernberg . |
| 5,306,286 | 4/1994 | Stack et al. . |
| 5,330,500 | 7/1994 | Song . |
| 5,342,348 | 8/1994 | Kaplan . |
| 5,342,621 | 8/1994 | Eury . |
| 5,356,433 | 10/1994 | Rowland et al. . |
| 5,383,928 | 1/1995 | Scott et al. ................................. 623/1 |
| 5,389,106 | 2/1995 | Tower . |
| 5,441,515 | 8/1995 | Khosravi et al. ....................... 606/194 |

OTHER PUBLICATIONS

"Biocompatibility of Glow–Discharge–Polymerized Films and Vacuum–Deposited Parylene," by Allen W. Hahn, et al., published by John M. Dalton Research Center, University of Missouri (1984).

"Fiber–Reinforced Absorbable Composite for Orthopedic Surgery," by R.A. Casper, B.S. Kelley, R.L. Dunn, A.G. Potter and D.N. Ellis in *Polymeric Materials Science and Engineering*, Proceedings of the ACS Division of Polymeric Materials: Science and Engineering, vol. 53, Fall Meeting 1985.

"Totally Resorbable High–Strength Composite Material," by Benjamin S. Kelley, Richard L. Dunn and Robert A. Casper, *Advances in Biomedical Polymers*, Edited by Charles G. Gebelein (1987).

"Electrical Insulation of Implantable Devices by Composite Polymer Coatings," by M.F. Nichols and A.W. Hahn, published by John M. Dalton Research Center, University of Missouri, as Paper No. 87–0110 (1987).

"Long–Term Implants of Parylene–C Coated Microelectrodes," by E.M. Schmidt, J.S. McIntosh and M.J. Bak, in *Medical & Biological Engineering & Computing*, Jan. 1988.

"Parylene, a Biostable Coating for Medical Applications," by Roger Olson, for NOVA TRAN Parylene Coating Services (Jul. 25, 1988, Nov. 14, 1988).

"A View of Vascular Stents," by Richard A. Schatz, M.D. from the Arizona Heart Institute Foundation, Phoenix, Arizona (1988).

"Advances in Coronary Angioplasty: Endovascular Stents," by David W.M. Muller and Stephen G. Ellis, M.D. in *Coronary Artery Disease*, Jul./Aug. 1990, vol. 1, No. 4.

"An Update on Coronary Stents," by Shing–Chiu Wong, M.D. and Richard A. Schatz, M.D. in *Cardio*, Feb. 1992.

"Parylene Coating for Medical Applications," by Victor A. Bull, in *Medical Product Manufacturing News*, Mar. 1993.

"Information Regarding Parylene C Coating for ACS Metal Stent," In–House Memorandum from Ed Newton to Joe Callol, Mike Clayman, Dennis Houlsby and Joe Tartaglia, dated Oct. 15, 1993 attaching Parylene, a Biostable Coating for Medical Applications, by Roger Olson.

Brochure entitled "Parylene Conformal Coating" by NOVA TRAN Custom Coating Services, a Subsidiary of Union Carbide Corporation (Undated).

POLYMER FILM FOR WRAPPING A STENT STRUCTURE

BACKGROUND OF THE INVENTION

1. Field of the Invention

This invention relates generally to expandable intraluminal vascular grafts, generally referred to as stents, and more particularly concerns metal stents wrapped with a polymer film capable of carrying and releasing therapeutic drugs.

2. Description of Related Art

Stents are typically implanted within a vessel in a contracted state and expanded when in place in the vessel in order to maintain patency of the vessel to allow fluid flow through the vessel. Ideally, implantation of such stents is accomplished by mounting the stent on the balloon portion of a catheter, positioning the stent in a body lumen, and expanding the stent to an expanded state by inflation of a balloon within the stent. The stent can then be left in place by deflating the balloon and removing the catheter.

Stents commonly have a metallic structure to provide the strength required to function as a stent, but typically do not provide for the delivery of localized therapeutic pharmacological treatment of a vessel at the location being treated with the stent. Polymeric materials capable of absorbing and releasing therapeutic agents may not fulfill the structural and mechanical requirements of a stent, especially when the polymeric materials are loaded with a drug, since drug loading of a polymeric material can significantly affect the structural and mechanical properties of the polymeric material. Since it is often useful to provide localized therapeutic pharmacological treatment of a vessel at the location being treated with the stent, it would be desirable to combine such polymeric materials with existing stent structures to provide a stent with the capability of absorbing therapeutic drugs or other agents, for placement and release of the therapeutic agents at a specific intravascular site. The present invention meets this need.

SUMMARY OF THE INVENTION

Briefly, and in general terms, the present invention provides for a stent wrapped with a polymer film capable of carrying and releasing therapeutic agents. Since the polymer film is wrapped on the outside of the stent, and is not needed to provide structural strength to assist in opening the flow path of the vasculature or other body lumen where the stent is to be placed, the drug-containing section can be specially formulated for its specific function of delivering drugs locally. The stent can be used in coronary arteries or any other part of the vasculature or other body lumen where mechanical opening force is necessary or desirable to keep the vessel open or to maintain the stent flush against the lumen wall, and where an anti-restenosis, anti-proliferative or other types of therapeutic drug or agent is to be simultaneously positioned and diffused.

The invention accordingly provides for a drug loaded stent, comprising an expandable stent structural member, and a planar sheet of polymeric material disposed on the outside of the expandable stent structural member. The polymeric material is preferably bioabsorbable, and is preferably loaded or coated or laminated with a therapeutic agent or drug to reduce or prevent restenosis and thrombosis in the vessel being treated. The polymer material can be a thermoplastic or an elastomer, for example, so that the film can stretch or deform radially when the stent structural member is expanded. The film of polymer material can be formed as a solid sheet, or can incorporate holes of various sizes and shapes to promote rapid endothelialization.

The polymer film is preferably mounted to the stent structural member, and in a presently preferred embodiment, the polymer film can be attached to the existing stent structural member in an unexpanded state by adhesive or by heat sealing, with the stent structural member sandwiched between internal and external layers of film heat sealed around the stent structural member, or mechanically, such as by mechanical connection such as by hooking one or more slots on an edge portion of the polymeric material through a corresponding slotted portion of the stent structural member, or with a metal clip. The polymer material can be attached to the stent structural member at one or more points, and wrapped in a coil around the stent in an unexpanded state, so that the diameter of the outer coiled film would uncoil and expand in diameter to match the diameter of the metal stent. When coiled around the stent structural member, the coiled polymer film can have at least one slit transverse to the longitudinal axis about which the stent is coiled to accommodate possible uneven expansion of the underlying stent structural member.

In another presently preferred embodiment, the polymer material can be attached to an existing stent structural member by an interference fit by tightly wrapping the polymer film at least once circumferentially around the stent structural member in an unexpanded state and attaching the polymer film to itself to form a sleeve around the stent structural member, such as by heating and melting the film to itself, adhesive bonding, solvent bonding, bonding one or more strips of elastic polymeric material on the outside edge of the polymeric film wrap to secure it, or by mechanical fastening, such as by a clip.

In one currently preferred embodiment, the polymer material can be attached to an existing stent structural member by hooking one or more slots on an edge portion of the polymeric material through a corresponding slotted portion of the stent structural member, tightly wrapping the polymer film at least once circumferentially around the stent structural member in an unexpanded state to form a coil of layers of the polymeric material, and securing the layers in a tightly wrapped coil. The coil is currently preferably secured to the stent structural member by adhesive bonding, typically by an adhesive such as a copolymer of poly-L-lactic acid (L-PLA) and polycaprolactone (PCL), although other adhesives, heat bonding, solvent bonding, or one or more mechanical fasteners, such as with a metal clip, for example, may also be suitable. Alternatively, the coil can be secured in a tightly wrapped coil by attaching one end of at least one piece of elastic material to an exterior end portion of the coil of polymeric material, and attaching the other end of the elastic material to a portion of the exterior of the wrapped coil of polymeric material. The elastic material stretches to allow the coil of polymeric material to uncoil as the stent is expanded.

In another currently preferred embodiment, a combination of a stent structural member and a polymeric film wrapping can be provided with a coating of lubricious material. The lubricious material currently preferably comprises a mixture of polyethylene oxide and polyethylene glycol, although other types of hydrophilic polymeric materials such as polyethylene acetate, polyvinyl pyrrolidone (PVP), polyvinyl alcohol, polyacrylamide, hydrophilic soft segment urethanes, some natural gums such as gum arabic, gum tragacanth and the like, polyanhydrides or other similar hydrophilic polymers, and combinations thereof, can also be used. The lubricious coating is currently preferably applied over a stent and polymer film wrap combination by dipping the wrapped stent in the hydrated, liquid lubricious material. The layer of lubricious material protects the stent from the guide or the body lumen in which the stent is inserted by providing a low friction surface over the stent.

These and other aspects and advantages of the invention will become apparent from the following detailed description, and the accompanying drawings, which illustrate by way of example the features of the invention.

DETAILED DESCRIPTION OF THE PREFERRED EMBODIMENTS

Stents that have a metallic structure typically do not provide for the delivery of localized therapeutic drugs in a blood vessel, while polymeric materials that can be used for drug delivery may not fulfill the structural and mechanical requirements of a stent to hold open a body lumen. Polymeric materials used for the dual function of structural support and for absorbing and releasing therapeutic agents may not fulfill either function satisfactorily, since drug loading of a polymeric material can significantly affect the structural and mechanical properties of the polymeric material, and the ability to absorb and release therapeutic agents or drugs can affect structural characteristics.

Accordingly, as shown in FIGS. 1–4, the present invention provides for a stent 20 that can be drug loaded, comprising an expandable stent structural member 22, and a planar sheet or film 24 of polymeric material, further described below, that in a first embodiment is attached to the metal stent at one or more points of attachment 26, and is wrapped in a coil around the stent in an unexpanded state. The polymer material can be extruded as a thin film, and any processing can be done while the material is a flat sheet.

Figures 1, 2, 3, 4:
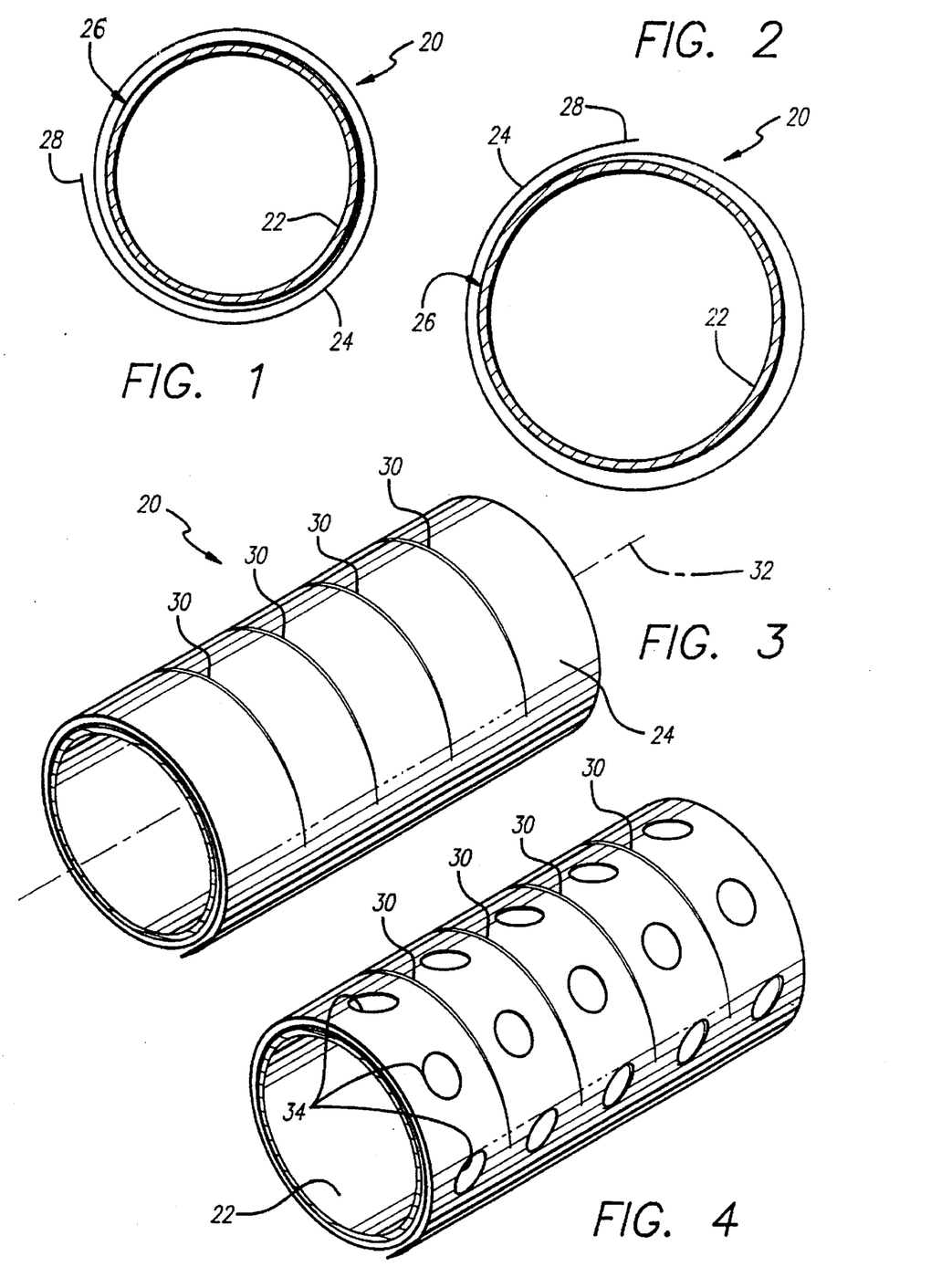
FIG. 1 is a cross-sectional view of a first embodiment of the stent structural member and film of polymer material of the drug loaded stent of the invention shown in an unexpanded state.
FIG. 2 is a cross-sectional view of the drug loaded stent of FIG. 1 shown in an expanded state.
FIG. 3 is a perspective view of the drug loaded stent of FIG. 1.
FIG. 4 is a perspective view of an alternate embodiment of the drug loaded stent of FIG. 1 having apertures in the exterior sheet of polymeric material.

The attachment of the film of polymeric material to the stent structural member in an unexpanded state can be by adhesive, heat sealing, such as with the stent structural member sandwiched between internal and external layers of film heat sealed or otherwise laminated around the stent structural member, by mechanical connection such as by hooking one or more slots on an edge portion of the polymeric material through a corresponding slotted portion of the stent structural member, as will be described further below, or with a metal clip, for example. The film of polymeric material also has a free end 28, and can have one or more slits 30 in the polymeric film transverse to the axis 32 of the stent to accommodate possible uneven expansion of the underlying stent structural member. The planar sheet of polymeric material is preferably adapted to uncoil and expand to match the expansion of the stent structural member. The planar sheet of polymeric material can be a solid sheet, or also can have a surface defining a plurality of apertures 34 of various sizes and shapes to promote rapid endothelialization, as is illustrated in FIG. 4. The stent can be mounted on a balloon dilatation catheter, for deployment of the stent in the vasculature of a patient.

Figure 5:
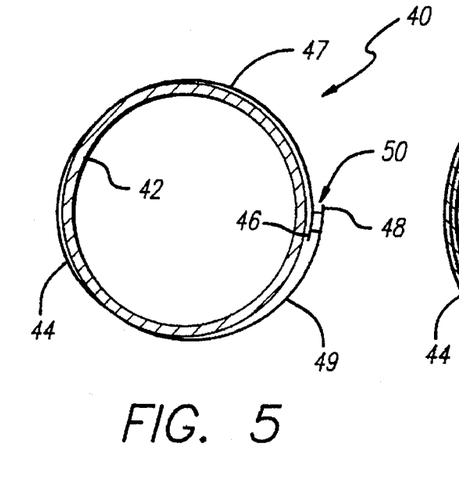
FIG. 5 is a cross-sectional view of a second embodiment of the drug loaded stent of the invention, shown in an unexpanded state.
Figure 7:
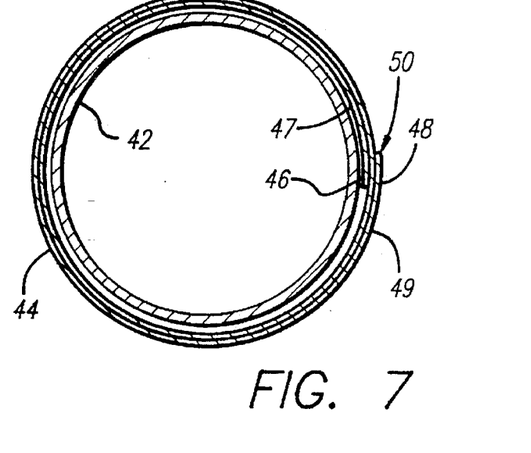
FIG. 7 is a cross-sectional view of an alternate embodiment of the drug loaded stent of FIG. 5 having multiple wrappings of the polymeric material.

As is illustrated in FIG. 5, in a second embodiment of the stent 40 that can be drug loaded, the stent comprises a stent metal structural member 42, and a planar sheet or film of polymeric material 44, further described below. The film of polymeric material in this embodiment has a first end 46 forming a first layer 47 of the polymeric material, and a second end 48 overlapping the first end forming a second layer 49 and attached to the first layer of the polymeric film, preferably by heating and melting the film to itself to form a longitudinal heat seal bond 50 between the first and second layers. Attachment of the two outer layers of the polymeric film can also be accomplished by adhesive bonding, solvent bonding, or one or more mechanical fasteners, such as with a metal clip, for example. In this embodiment, the planar sheet of polymeric material is preferably wrapped circumferentially and cinched tightly as a sleeve around the stent structural member, and is thus attached to the stent structural member by interference fit. In an alternative embodiment illustrated in FIG. 7, the polymeric material can be wrapped multiple times around the stent to form multiple layers that can be joined together as described with reference to FIG. 5 to form a tube around the stent. Alternatively, the polymeric material can be formed as a seamless tube or sleeve to fit tightly around the unexpanded stent structural member.

The primary function of the sheet of polymeric material is to deliver therapeutic agents or drugs to help prevent thrombosis and/or restenosis. The planar sheet of polymeric material is preferably selected from the group of polymers consisting of thermoplastic and elastomeric polymers, so that the polymeric film can stretch or deform radially when the stent structural member is expanded.

Figure 6:
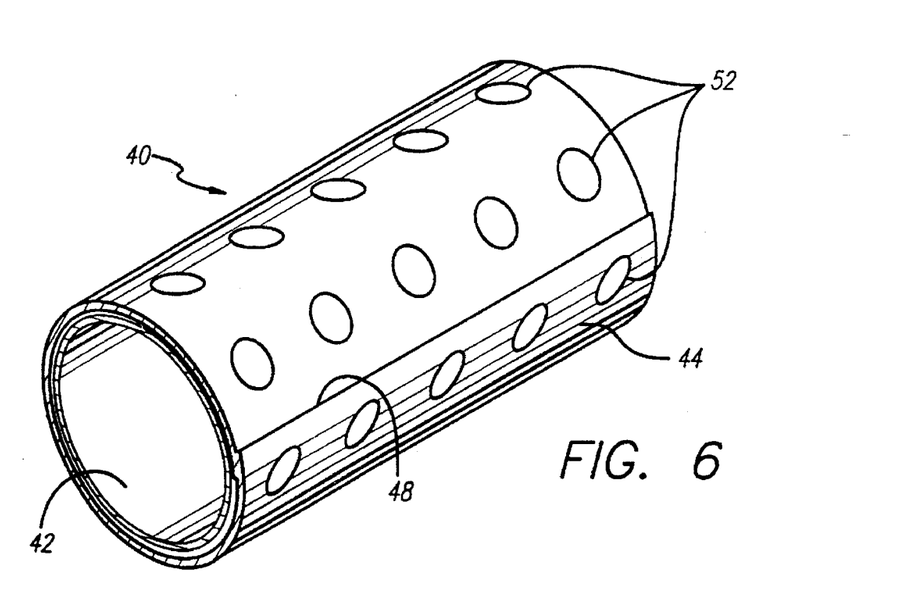
FIG. 6 is a perspective view of an alternate embodiment of the drug loaded stent of FIG. 5 having apertures in the polymeric material.

As is shown in FIG. 6, the planar sheet of polymeric material also can have a surface defining a plurality of apertures 52 of various sizes and shapes to promote rapid endothelialization, similar to the embodiment illustrated in FIG. 4. The stent can be mounted on a balloon dilatation catheter, for deployment of the stent in the vasculature of a patient.

Figure 8:
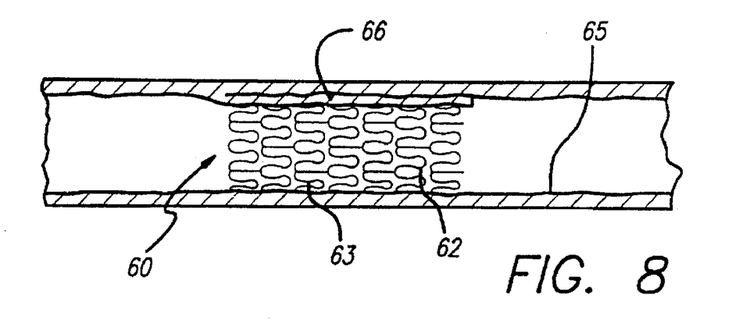
FIG. 8 is an elevational view of a representative stent structural member, shown in a vessel.

In each of these embodiments, the stent structural member is of the type that can be implanted within a vessel in a contracted state and expanded to maintain patency of the vessel and to allow fluid flow through the vessel, such as expanding stents available from Advanced Cardiovascular Systems, Inc., Santa Clara, Calif., (ACS), Palmaz-Shatz (Johnson and Johnson), Gianturco (Cook Incorporated), and the like. The metal structural member can, for example, be formed from a metal selected from the group of metals consisting of stainless steel, MP35N, MP20N, elastinite (nitinol), tantalum, nickel-titanium alloy, platinum-iridium alloy, gold, and magnesium, although the stent structural member can also be formed of suitable non-metallic materials. "MP35N" and "MP20N" are trade names for alloys of cobalt, nickel, chromium and molybdenum available from Standard Pressed Steel Co. of Jenkintown, Pa.. MP35N consists of 35% cobalt, 35% nickel, 20% chromium, and 10% molybdenum. MP20N consists of 50% cobalt, 20% nickel, 20% chromium, and 10% molybdenum. A representative stent structural member 60 with which a sheet of polymeric material can be combined according to the principles of the invention is illustrated in FIG. 8. In one preferred embodiment, the stent structural member 60 can be formed of metal, and comprises a plurality of radially expandable cylindrical elements 62 disposed coaxially and interconnected by members 63 disposed between adjacent cylindrical elements. The stent structural member is shown without a covering sheet of polymeric material, in a typical setting within a vessel 65, for repairing a detached vessel lining 66, for example, and maintaining the patency of the vessel.

The polymeric material is preferably selected from thermoplastic and elastomeric polymers. In one currently preferred embodiment the polymeric material can be a material available under the trade name "C-Flex" from Concept Polymer Technologies of Largo, Fla. In another currently preferred embodiment, the polymeric material can be ethylene vinyl acetate (EVA); and in yet another currently preferred embodiment, the polymeric material can be a material available under the trade name "BIOSPAN." Other suitable polymeric materials include latexes, urethanes, polysiloxanes, and modified styrene-ethylene/butylene-styrene block copolymers (SEBS) and their associated families, as well as elastomeric, bioabsorbable, linear aliphatic polyesters. The polymeric material can typically have a thickness in the range of about 0.002 to about 0.020 inches, for example. The polymeric material is preferably bioabsorbable, and is preferably loaded or coated with a therapeutic agent or drug, including, but not limited to, antiplatelets, antithrombins, cytostatic and antiproliferative agents, for example, to reduce or prevent restenosis in the vessel being treated. The therapeutic agent or drug is preferably selected from the group of therapeutic agents or drugs consisting of sodium heparin, low molecular weight heparin, hirudin, argatroban, forskolin, vapiprost, prostacyclin and prostacyclin analogues, dextran, D-phe-pro-arg-chloromethylketone, dipyridamole, glycoprotein IIb/IIIa platelet membrane receptor antibody, recombinant hirudin, thrombin inhibitor, angiopeptin, angiotensin converting enzyme inhibitors, (such as Captopril, available from Squibb; Cilazapril, available for Hoffman-La Roche; or Lisinopril, available from Merck) calcium channel blockers, colchicine, fibroblast growth factor antagonists, fish oil, omega 3-fatty acid, histamine antagonists, HMG-CoA reductase inhibitor, methotrexate, monoclonal antibodies, nitroprusside, phosphodiesterase inhibitors, prostaglandin inhibitor, seramin, serotonin blockers, steroids, thioprotease inhibitors, triazolopyrimidine and other PDGF antagonists, alpha-interferon and genetically engineered epithelial cells, and combinations thereof. While the foregoing therapeutic agents have been used to prevent or treat restenosis and thrombosis, they are provided by way of example and are not meant to be limiting, as other therapeutic drugs may be developed which are equally applicable for use with the present invention.

In another currently preferred embodiment illustrated in FIGS. 9–13, the stent 70 that can be drug loaded comprises a stent metal structural member 72, such as the stent structural member 70 illustrated for example in FIG. 8, and a planar sheet or film of polymeric material 74, preferably including a plurality of apertures 88, as will be further explained below. The polymeric material can be attached to an existing stent structural member by tightly wrapping the polymer film at least once, and preferably multiple times, circumferentially around the stent structural member 72 in an unexpanded state to form a coil of layers of the polymeric material. The film of polymeric material in this embodiment has an interior end 76, multiple wrappings forming a plurality of layers 77 of the polymeric material, and an exterior end 78 overlapping the multiple layers. The coil of polymeric material is preferably secured snugly over the stent structure by at least one piece or strip of elastic material 80. One end 82 of at least one such piece or strip of elastic material is attached to the exterior end portion 78 of the coil of polymeric material, and an opposing end 83 of the piece of elastic material is attached to another portion 84 of the exterior of the wrapped coil of polymeric material, across edge of the exterior end portion 78 of the coil of polymeric material, to secure the coil on the stent. In one currently preferred embodiment illustrated in FIGS. 9–11, the coil of polymeric material can be advantageously secured on the stent structural member by two strips of such elastic material. Additional strips of elastic material can also be used to secure the coil of polymeric material, as needed. The elastic material stretches to allow the coil of polymeric material to uncoil as the stent is expanded. In a currently preferred embodiment, the strips of elastic material are heat bonded to the coil of polymeric material. Attachment of the elastic material can also be accomplished by adhesive bonding, solvent bonding, or one or more mechanical fasteners, such as with a metal clip, for example. In this embodiment, the planar sheet of polymeric material is preferably wrapped circumferentially and cinched tightly as a sleeve around the stent structural member, and is thus attached to the stent structural member by interference fit.

Figure 9:
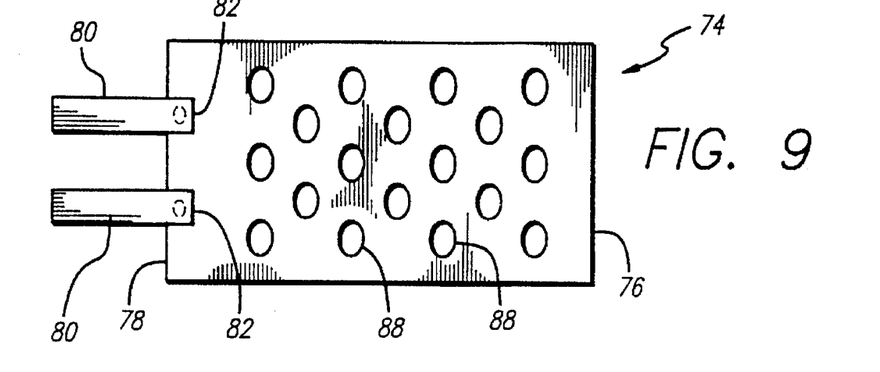
FIG. 9 is a plan view of a sheet of polymeric material in another alternative embodiment including elastic strips for securing the polymeric material wrapped around a stent structural member.
Figure 10:
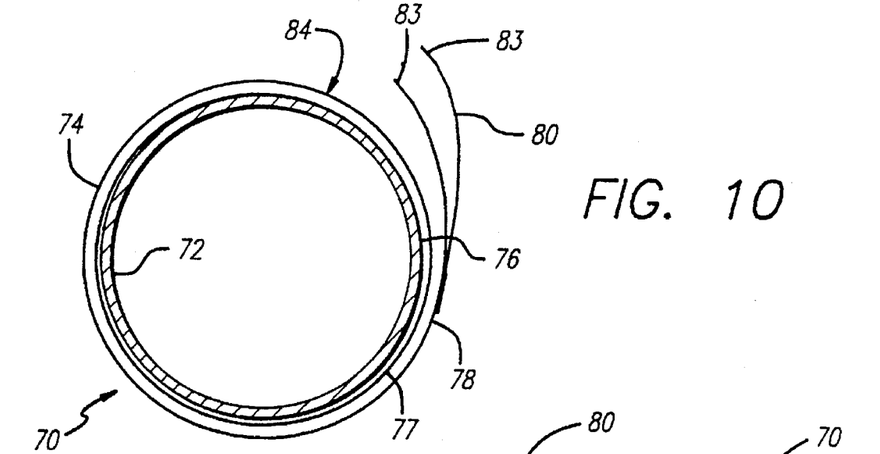
FIG. 10 is a cross-sectional view of a drug loaded stent wrapped with the polymeric material of FIG. 9.
Figure 11:
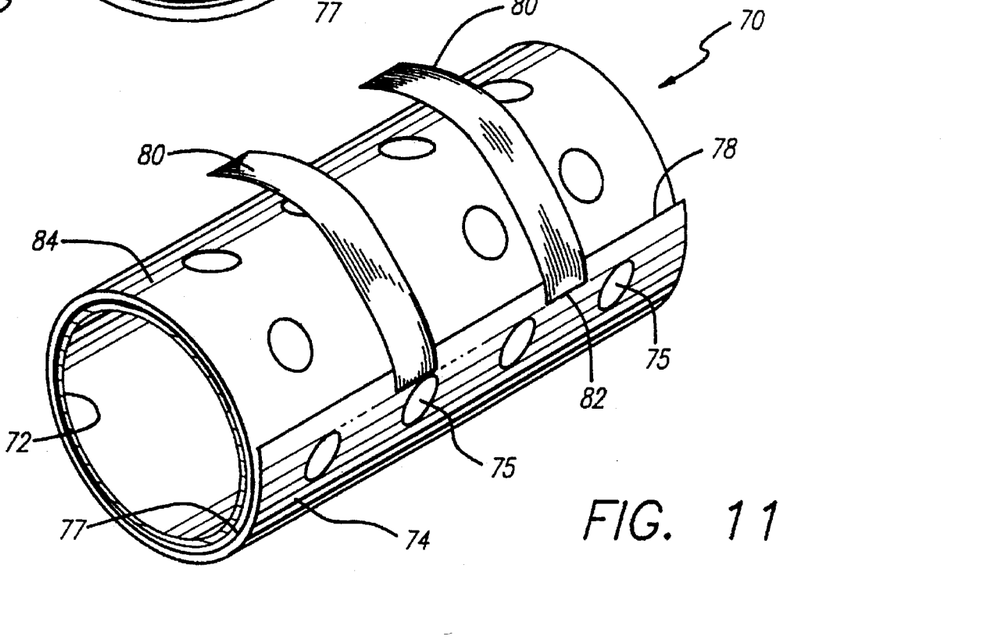
FIG. 11 is a perspective view of the drug loaded stent of FIG. 10.
Figure 12:
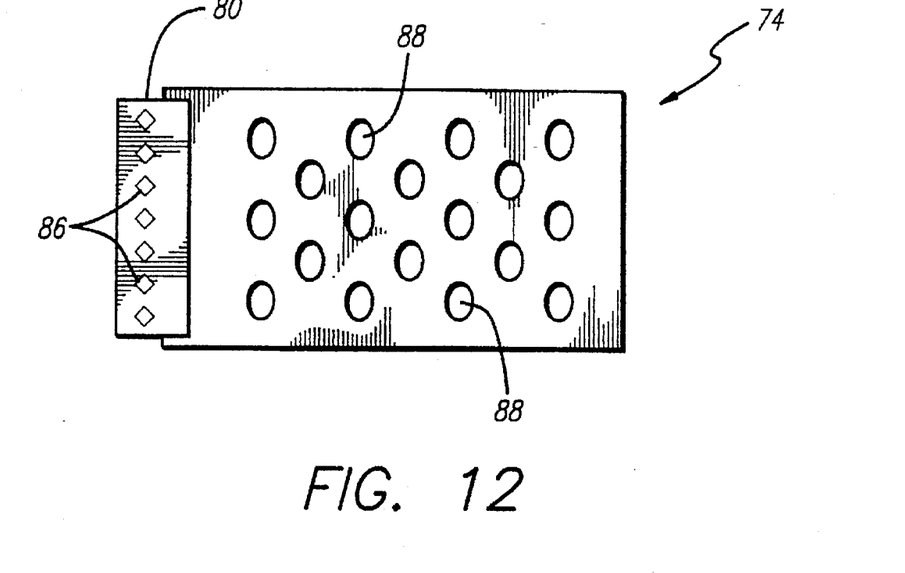
FIG. 12 is a plan view of a sheet of polymeric material in a further alternative embodiment including an elastic strip extending the width of the polymeric material for securing the polymeric material when wrapped around a stent structural member.
Figure 13:
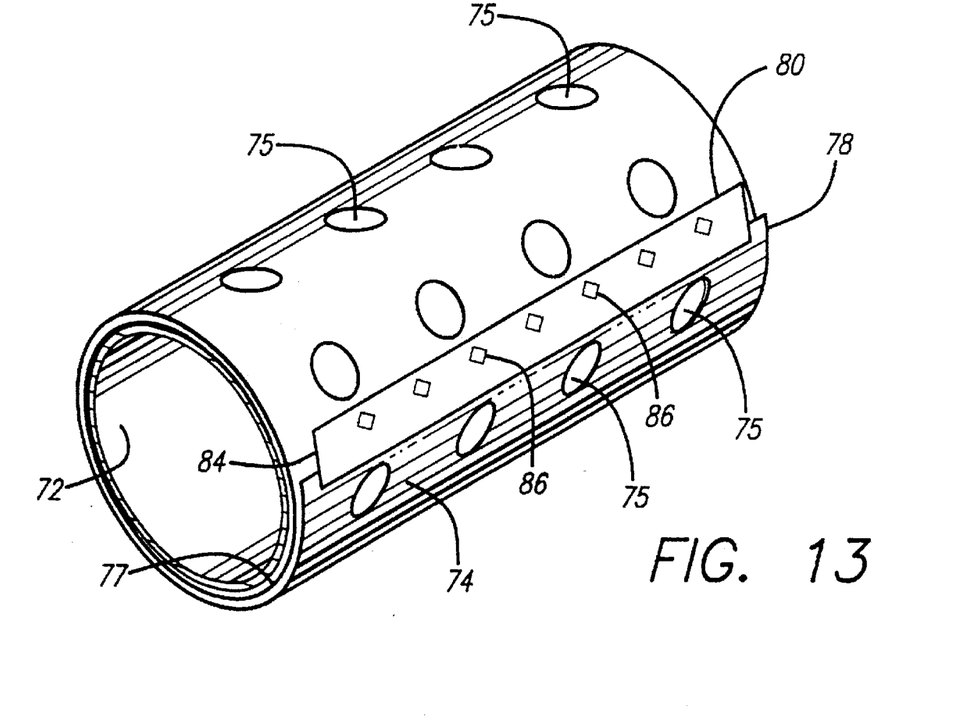
FIG. 13 is a perspective view of a drug loaded stent wrapped with the polymeric material of FIG. 12.

In a currently preferred alternative embodiment shown in FIGS. 12 and 13, similar to that illustrated in FIGS. 9–11, the elastic strip of material 80 can extend and be bonded along the entire width of the exterior end 78 of the coil of polymeric material as is shown in FIG. 12, and can be bonded to the other portion 84 of the exterior of the wrapped coil of polymeric material, across the edge of the exterior end portion 78 of the coil of polymeric material, to secure the coil on the stent, as is illustrated in FIG. 13. The strip of elastic material can also be perforated, such as with apertures 86 formed in the strip of elastic material for example, to decrease the cross-sectional area of the elastic material, to permit the elastic material to stretch more easily. The polymeric film material also currently preferably includes a plurality of apertures 88 so that the polymeric material is porous, to allow blood flow through the stent structural member to the vessel wall, such as for oxygenation and nutrient exchange to the vessel wall, and in order to present a decreased surface area for purposes of reducing thrombogenicity. The apertures also improve the flexibility of the polymeric material, allowing the stent segment to be more easily rolled and uncoiled during expansion of the stent structural member, and also facilitate the process of cell growth over the surface of the stent.

The primary function of the sheet of polymeric material is to deliver therapeutic agents or drugs to help prevent thrombosis and/or restenosis. The planar sheet of polymeric material is preferably selected from the group of polymers consisting of thermoplastic and elastomeric polymers, that however can be substantially inelastic, so as not to lose a significant part of their thickness during expansion of the stent structural member, such as polycaprolactone, for example, allowing a high upper threshold for the amount of one or more drugs that can be loaded in the polymeric material and delivered. The inelastic polymeric material currently preferably is of a thickness that will guarantee drug delivery over at least approximately a seven day period, which is not currently possible with radially expanding elastic films. In the embodiment illustrated in FIGS. 9–13, an inelastic drug loaded polymeric material is currently preferably no greater than about 0.002 inch thick, and typically approximately 0.0015 inch to 0.002 inch thick, to prevent the profile of the stent and wrap of polymeric material from becoming too large. The elastic portion of the sleeve of polymeric material keeps the coiled polymeric film secured snugly over the expandable stent structural member, so that the polymeric material can be applied over the stent structural member without the need for additional internal points of attachment to the stent structural member. The elastic portion of the sleeve of polymeric material also keeps tension on the coiled, inelastic drug-containing material while the stent structural member is expanding, without providing so much resistance so as to impede expansion of the stent structural member, or the unrolling of the inelastic polymeric material.

The elastic strip of material can be joined on the interior or exterior of the end portion of the coiled polymeric material. The elastic material attached over the coil of polymeric material helps keep the coil of drug loaded material snug on the stent structural member before it is expanded, and guides its linear expansion during inflation of a balloon dilatation catheter used for deployment of the stent and polymeric drug loaded material in the vasculature or other body lumen of a patient.

The elastic material is currently typically formed of ethylene vinyl acetate, but can also be formed of silicone polymers. The drug loaded layer of polymeric material, and the stent structural member can be formed of the materials as described above in the previous embodiments.

Figures 14, 15:
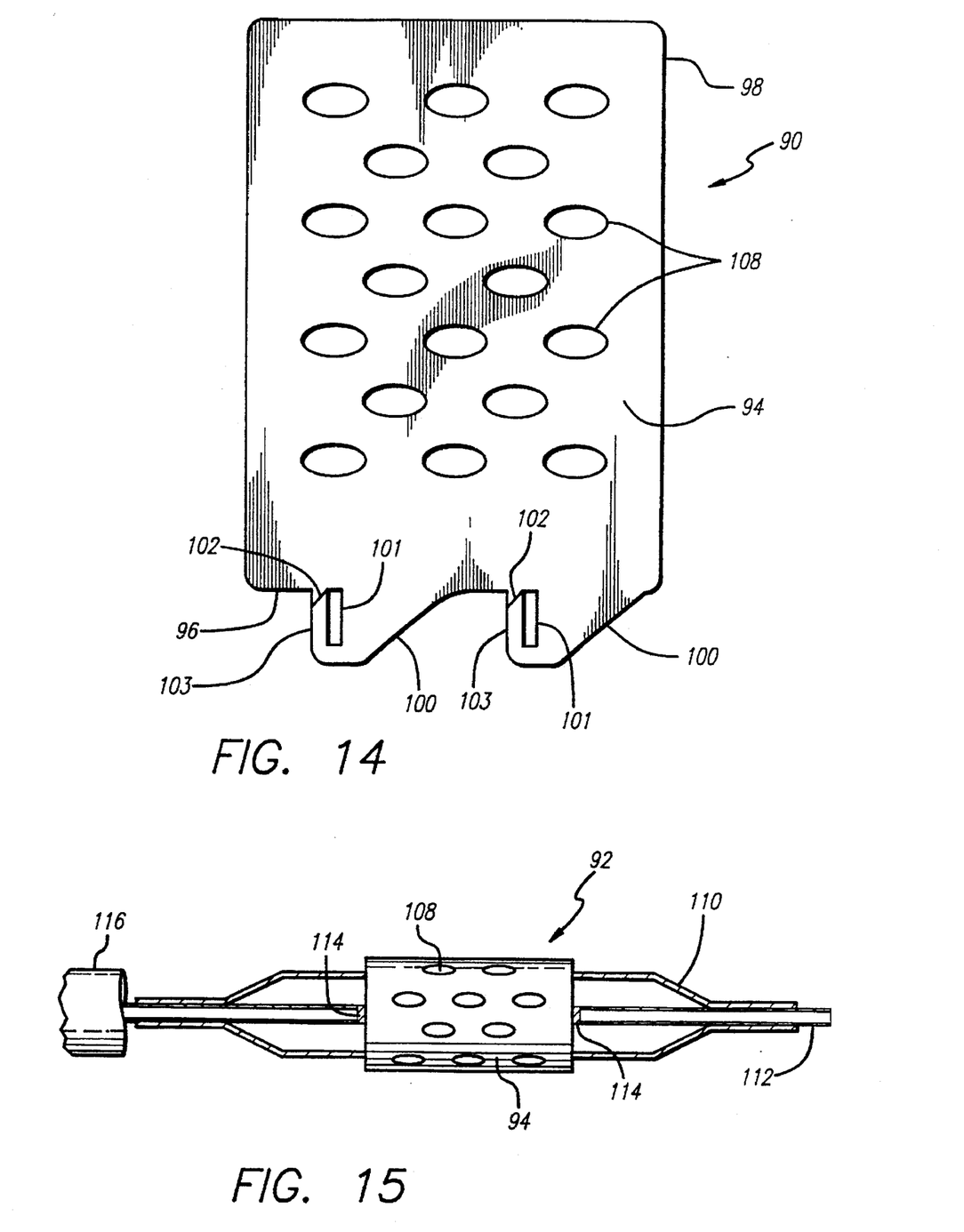
FIG. 14 is a plan view of a sheet of polymeric material in a further alternative embodiment including attachment tabs for securing the polymeric material to a stent structural member.
FIG. 15 is an elevational view of a drug loaded stent wrapped with the sheet of polymeric material of FIG. 14 and mounted on a balloon dilatation catheter for delivery.
Figure 16:
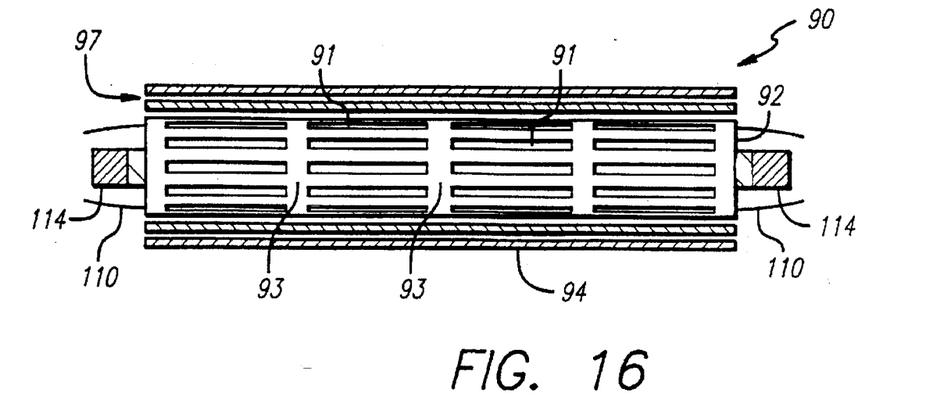
FIG. 16 is an enlarged partial sectional view of the drug loaded stent of FIG. 15 showing the sheet of polymeric material wrapped around a slotted tube stent structural member.

In another alternative embodiment illustrated in FIGS. 14–16, another preferred type of stent 90 that can be drug loaded comprises a stent metal structural member 92, that can for example be a slotted tube type of stent having a plurality of slotted openings 91 and structural ribs 93 as is illustrated in FIG. 16, such as is available from ACS for example, in combination with a planar sheet or film of polymeric material 94. The stent structural member can also be other types of stents that preferably have a relatively significant proportion of space provided by openings, slots, or the like in the otherwise solid material of the stent structure. The polymeric material can be attached to such a stent structural member by tightly wrapping the polymer film at least once, and preferably multiple times, circumferentially around the stent structural member 92 in an unexpanded state to form a coil of layers of the polymeric material. The film of polymeric material in this embodiment has an interior end 96 with at least one attachment member or tab 100 adapted to be received in openings 91 of the stent structural member and thereby attached to the stent structural member, and provides multiple wrappings forming a plurality of layers 97 of the polymeric material, with an exterior end 98 overlapping the interior multiple layers. As is shown in FIG. 14, the polymeric film of material currently preferably has a plurality of attachment tabs 100, and typically has two of the attachment tabs. Each attachment tab currently preferably includes an aperture 101 therethrough adapted to receive and hook onto a structural rib portion 93 of the stent structural member. The attachment tab also includes a slit 102 extending from the aperture 101 to the outer edge 103 of the attachment tab to allow the attachment tab to be hooked onto the stent structural member. After the attachment tab is hooked onto a portion of the stent structural member, the slit 102 is preferably sealed closed, such as by application of an adhesive material, typically a copolymer of poly-L-lactic acid (L-PLA) and polycaprolactone (PCL), other suitable adhesives, or by heat bonding. The coil of polymeric material is preferably formed of a thermoplastic material such as polycaprolactone that can be drug loaded, and can be wrapped and secured snugly over the stent structure by heat bonding the exterior end 98 to another portion of the exterior of the wrapped coil of polymeric material as described above. The polymeric film of material tensions the attachment tabs as the stent structural member is expanded and as the wrapping of polymeric material uncoils, to bias the attachment tab extending into the lumen of the stent structural member against the inner surface of the lumen of the stent structural member to ensure that the attachment tabs do not obstruct the lumen within the stent structural member. Attachment of the exterior edge of the polymeric material to the wrapping of polymeric material is currently preferably accomplished by adhesive bonding, typically by an adhesive such as a copolymer of poly-L-lactic acid (LPLA) and polycaprolactone (PCL), although other adhesives, heat bonding, solvent bonding, or one or more mechanical fasteners, such as with a metal clip, for example, may also be suitable.

In a currently preferred embodiment, the polymeric film material is typically about 0.002 inch thick, and also currently preferably includes a plurality of apertures 108 so that the polymeric material is porous, to allow blood flow through the stent structural member to the vessel wall, such as for oxygenation and nutrient exchange to the vessel wall, and in order to present a decreased surface area for purposes of reducing thrombogenicity. The apertures also improve the flexibility of the polymeric material, allowing the stent segment to be more easily rolled and uncoiled during expansion of the stent structural member, and also facilitate the process of cell growth over the surface of the stent.

The primary function of the sheet of polymeric material is to deliver therapeutic agents or drugs to help prevent thrombosis and/or restenosis. The planar sheet of polymeric material is preferably selected from the group of polymers consisting of thermoplastic and elastomeric polymers that may be inelastic, and that do not lose a significant part of their thickness during expansion of the stent structural member, allowing a high upper threshold for the amount of one or more drugs that can be loaded in the polymeric material and delivered. As is illustrated in FIGS. 15 and 16, the drug loaded stent can be mounted on an expandable balloon member 110 of a dilatation catheter 112, near radiopaque markers 114 of the catheter, for delivery of the stent in an artery, blood vessel, or other body lumen, such as through a protective sheath 116, shown cutaway for convenience of illustration.

Figure 17:
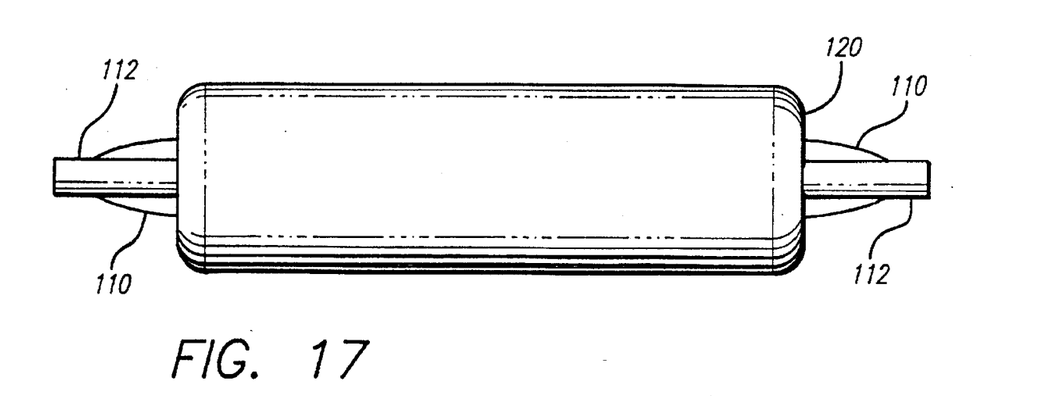
FIG. 17 is an elevational view of the drug loaded stent of FIG. 15 covered with a layer of a lubricious, hydrophilic polymeric coating.
Figure 18:
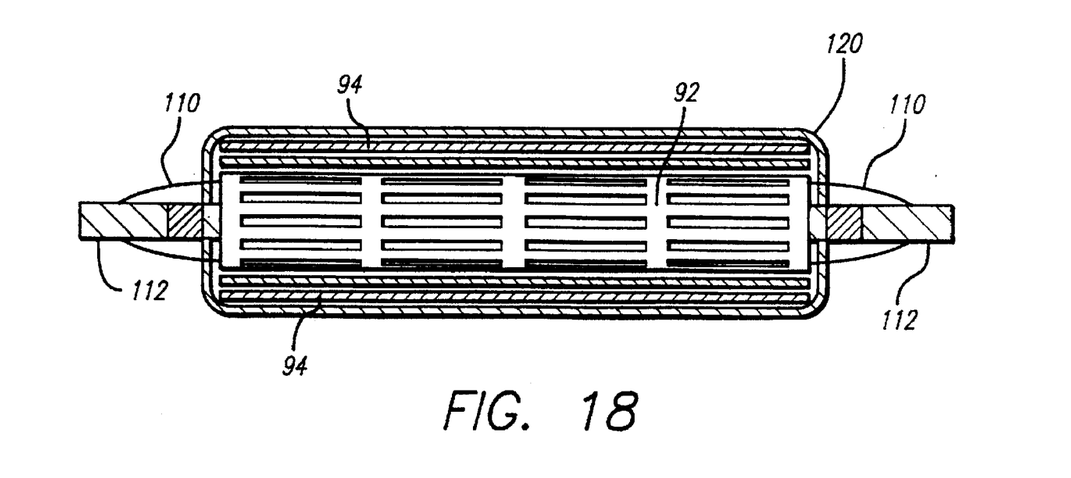
FIG. 18 is a partial sectional view of the drug-loaded stent of FIG. 17.

In another currently preferred embodiment illustrated in FIGS. 17–18, a combination of a stent structural member and a polymeric film wrapping can be provided with a coating of lubricious material 120. The lubricious material currently preferably comprises a mixture of polyethylene oxide and polyethylene glycol, providing both high and low molecular weight components in the lubricious material, although other types of hydrophilic polymeric materials such as polyethylene acetate, polyvinyl pyrrolidone (PVP), polyvinyl alcohol, polyacrylamide, hydrophilic soft segment urethanes, some natural gums such as gum arabic or gum tragacanth and the like, polyanhydrides or other similar hydrophilic polymers, and combinations thereof, can also be used. The lubricious material can also carry an anti-thrombogenic drug that can be the same as, or complementary to, the anti-thrombogenic or antiproliferative drug or drugs carried in the polymeric material of the stent.

The lubricious coating is currently preferably applied over a stent and polymer film wrap combination by dipping the wrapped stent in the hydrated, liquid lubricious material. The lubricious material is typically prepared to be sufficiently viscous to allow the stent to be sufficiently coated by a single dipping. The lubricious coating is initially quite sticky when applied, but is dried to provide a non-sticky tight cocoon around the wrapped stent, and helps to keep the polymer wrapping tight. While the lubricious coating is shown applied to a wrapped stent such as that of FIGS. 14–16, the lubricious coating can advantageously be applied to any of the foregoing wrapped stent combinations, and other suitable stents as well. The lubricious coating becomes hydrated again upon exposure to the blood during delivery of the stent. When a sheath is used in the delivery system to protect the stent during delivery, the lubricious coating can be initially hydrated before contacting the blood by flushing the sheath with saline solution. Due to the gel-like nature of the lubricious coating, the lubricious coating eventually dissolves in a short period of time, and will typically be completely degraded and dissolved by the time that the stent is deployed and expanded.

The layer of lubricious material protects the stent from the guide or the anatomy by providing a low friction surface over the stent. If a sheath or sleeve is used for delivering the stent, the lubricious coating aids in retraction of the sheath by decreasing friction between internal and external layers of the delivery system. The deployment of the stent can also be improved by decreasing friction between the stent and the balloon used to deliver the stent, decreasing friction between the layers of the stent itself, or decreasing friction between the vessel or lumen wall and the stent. The need for a sheath for protecting the stent during delivery can also be mitigated if the coating is of a thickness suited to providing a smooth transition through the delivery system, and still provides a low profile of the uninflated, undeployed stent. Alternatively, the lubricious coating can also be formed as a dried sheet of lubricious material, cut into a strip, wrapped in spiral fashion over the length of the polymeric drug carrying wrapping, and bonded in place by an adhesive such as a copolymer of poly-L-lactic acid (L-PLA) and polycaprolactone (PCL), although other adhesives, or heat bonding may also be suitable.

It has thus been demonstrated that the invention provides for a stent combining polymeric materials with stent structures with the capability of absorbing therapeutic drugs or other agents, for placement and release of the therapeutic agents at a specific intravascular site. A complex locking design is not needed, and the stent can be re-dilated if necessary. The polymeric, drug-containing section can be bioabsorbable, and can be specially formulated for its specific function of delivering drugs locally, since it is not necessary for the polymeric component to provide assistance in keeping the blood vessel open. The polymeric material can be extruded as a film, using simple technology, and can be processed while the material is a flat sheet. The stent can be used in coronary arteries or any other part of the vasculature where mechanical opening force is necessary or desirable to keep the vessel open, and where anti-restenosis, anti-proliferative or other types of therapeutic drugs or agents can be useful in combatting thrombosis and restenosis.

It will therefore be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. A drug loaded stent, comprising:
   an expandable stent structural member; and
   a sheet of polymeric material having one end attached to the stent structural member and a free end, said sheet of polymeric material being wrapped in a coil about the stent, whereby said sheet of polymeric material is free to uncoil when said stent structural member is expanded, to substantially match the expansion of said stent structural member, said polymeric material being loaded with a therapeutic agent.

2. The drug loaded stent of claim 1, wherein said sheet of polymeric material is wrapped circumferentially around the stent structural member at least one time, and said sheet of polymeric material is attached to the stent structural member by adhesive.

3. The drug loaded stent of claim 1, wherein said stent structural member has a surface defining a plurality of slotted openings therethrough and a plurality of structural ribs, said sheet of polymeric material has at least one attachment tab having an aperture therethrough and a slit extending from said aperture to an outside edge of said attachment tab, said sheet of polymeric material being attached to the stent structural member by inserting said attachment tab into one said stent slotted opening and hooking said slit and said aperture of said attachment tab to a structural rib of said stent structural member, and said sheet of polymeric material is wrapped circumferentially around the stent structural member at least one time.

4. The drug loaded stent of claim 1, wherein said stent structural member has a longitudinal axis, and said sheet of polymeric material has at least one slit transverse to the axis of said stent structural member to accommodate uneven expansion of the stent structural member.

5. The drug loaded stent of claim 1, wherein said therapeutic agent is selected from the group consisting of therapeutic agents consisting of antiplatelets, antithrombins, cytostatic and antiproliferative agents.

6. The drug loaded stent of claim 1, wherein said therapeutic agent is selected from the group of therapeutic agents consisting of sodium heparin, low molecular weight heparin, hirudin, argatroban, forskolin, vapiprost, prostacyclin, prostacyclin analogues, dextran, D-phe-pro-arg-chloromethylketone, dipyridamole, glycoprotein IIb/IIIa platelet membrane receptor antibody, recombinant hirudin, thrombin inhibitor, angiopeptin, angiotensin converting enzyme inhibitors, calcium channel blockers, colchicine, fibroblast growth factor antagonists, fish oil, omega 3-fatty acid, histamine antagonists, HMG-CoA reductase inhibitor, methotrexate, monoclonal antibodies, nitroprusside, phosphodiesterase inhibitors, prostaglandin inhibitor, serotonin blockers, steroids, thioprotease inhibitors, triazolopyrimidine, PDGF antagonists, alpha-interferon, genetically engineered epithelial cells, and combinations thereof.

7. The drug loaded stent of claim 1, wherein said stent structural member is formed from a metal selected from the group of metals consisting of stainless steel, tantalum, nickel-titanium alloy, platinum-iridium alloy, gold, magnesium, an alloy consisting essentially of about 35 percent cobalt, about 35 percent nickel, about 20 percent chromium, and about 10 percent molybdenum and an alloy consisting essentially of about 50 percent cobalt, about 20 percent nickel, about 20 percent chromium, and about 10 percent molybdenum.

8. The drug loaded stent of claim 1, wherein said sheet of polymeric material has a surface defining a plurality of openings to promote rapid endothelialization.

9. The drug loaded stent of claim 1, wherein said sheet of polymeric material is coated with a layer of hydrophilic lubricious polymeric material.

10. The drug loaded stent of claim 9, wherein said lubricious material is selected from the group consisting of polyethylene oxide, polyethylene glycol, polyethylene acetate, polyvinyl pyrrolidone, polyvinyl alcohol, polyacrylamide, hydrophylic soft segment urethane, gum arabic, gum tragacanth, and combinations thereof.

* * * * *